United States Patent [19]

Yamaguchi

[11] Patent Number: 5,433,740
[45] Date of Patent: Jul. 18, 1995

[54] METHOD AND APPARATUS FOR THERMOTHERAPY

[75] Inventor: Seiji Yamaguchi, Tokyo, Japan

[73] Assignee: Olympus Optical Co., Ltd., Tokyo, Japan

[21] Appl. No.: 149,126

[22] Filed: Nov. 5, 1993

Related U.S. Application Data

[63] Continuation of Ser. No. 845,625, Mar. 4, 1992, abandoned.

[30] Foreign Application Priority Data

Apr. 25, 1991 [JP] Japan .................................. 3-095869

[51] Int. Cl.⁶ .............................................. A61N 5/00
[52] U.S. Cl. ...................................... 607/102; 607/113
[58] Field of Search .......................... 128/736; 601/15; 607/96, 98, 99, 102–105, 108, 113

[56] References Cited

U.S. PATENT DOCUMENTS

| | | | |
|---|---|---|---|
| 4,676,258 | 6/1987 | Inokuchi et al. | 128/804 |
| 4,747,416 | 5/1988 | Kikuchi et al. | |
| 4,867,175 | 9/1989 | Takase | 128/804 |
| 4,907,589 | 3/1990 | Cosman | 128/401 |
| 4,960,109 | 10/1990 | Lele | 128/736 |
| 4,961,422 | 10/1990 | Marchosky et al. | 128/401 |
| 5,003,991 | 4/1991 | Takayama et al. | 128/804 |
| 5,026,959 | 6/1991 | Ito et al. | 128/401 |
| 5,106,360 | 4/1992 | Ishiwara et al. | 128/401 |
| 5,168,880 | 12/1992 | Sagawa et al. | 128/401 |
| 5,234,004 | 8/1993 | Hascoet et al. | 128/736 X |

FOREIGN PATENT DOCUMENTS 61-58671 3/1986 Japan .
61-58672 3/1986 Japan .

*Primary Examiner*—Lee S. Cohen
*Assistant Examiner*—Samuel Gilbert
*Attorney, Agent, or Firm*—Frishauf, Holtz, Goodman & Woodward

[57] ABSTRACT

An apparatus for thermotherapy has a plurality of temperature sensors to control a temperature-elevating energy output for allowing temperature which is detected at the temperature sensors to be set to be within a predetermined temperature range. To this end, the apparatus is adapted to select one or a plurality of temperature sensors which are detected at different sites in an area including an affected region to be temperature-elevated, to compare measured data of the selected temperature sensor with predetermined temperature data and to control a temperature-elevating output on the basis of a result of comparison.

14 Claims, 13 Drawing Sheets

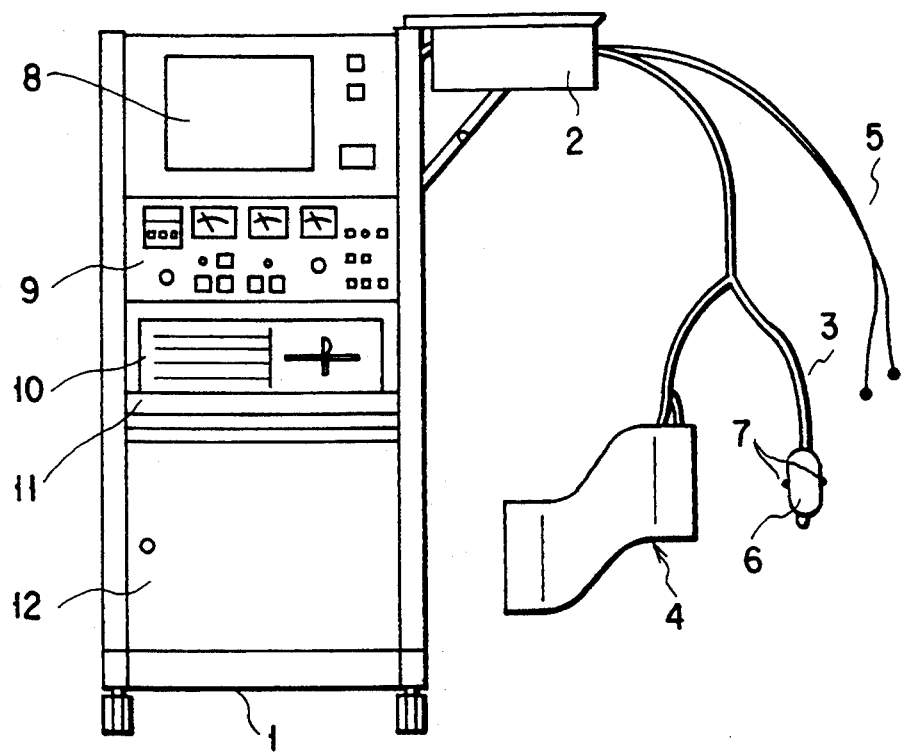
F I G. 1
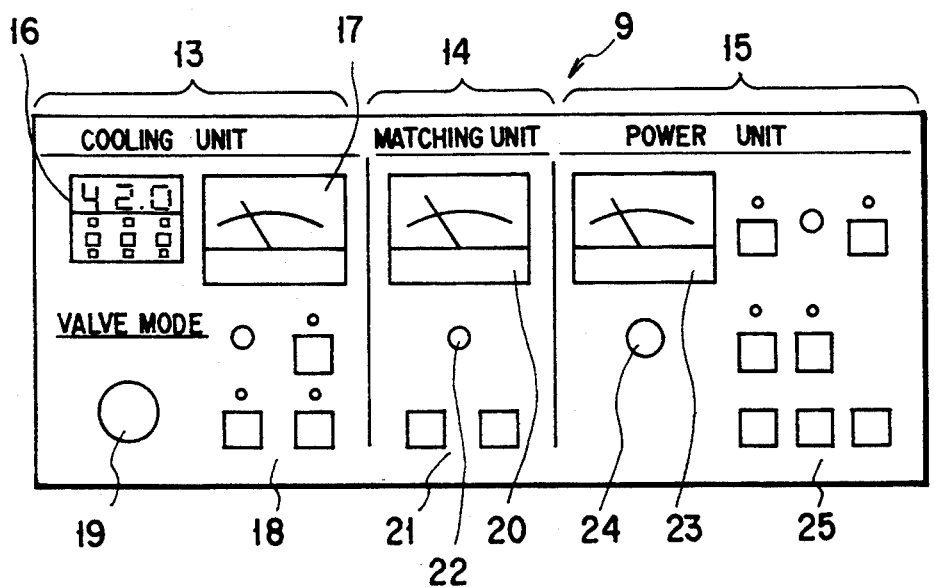
F I G. 2

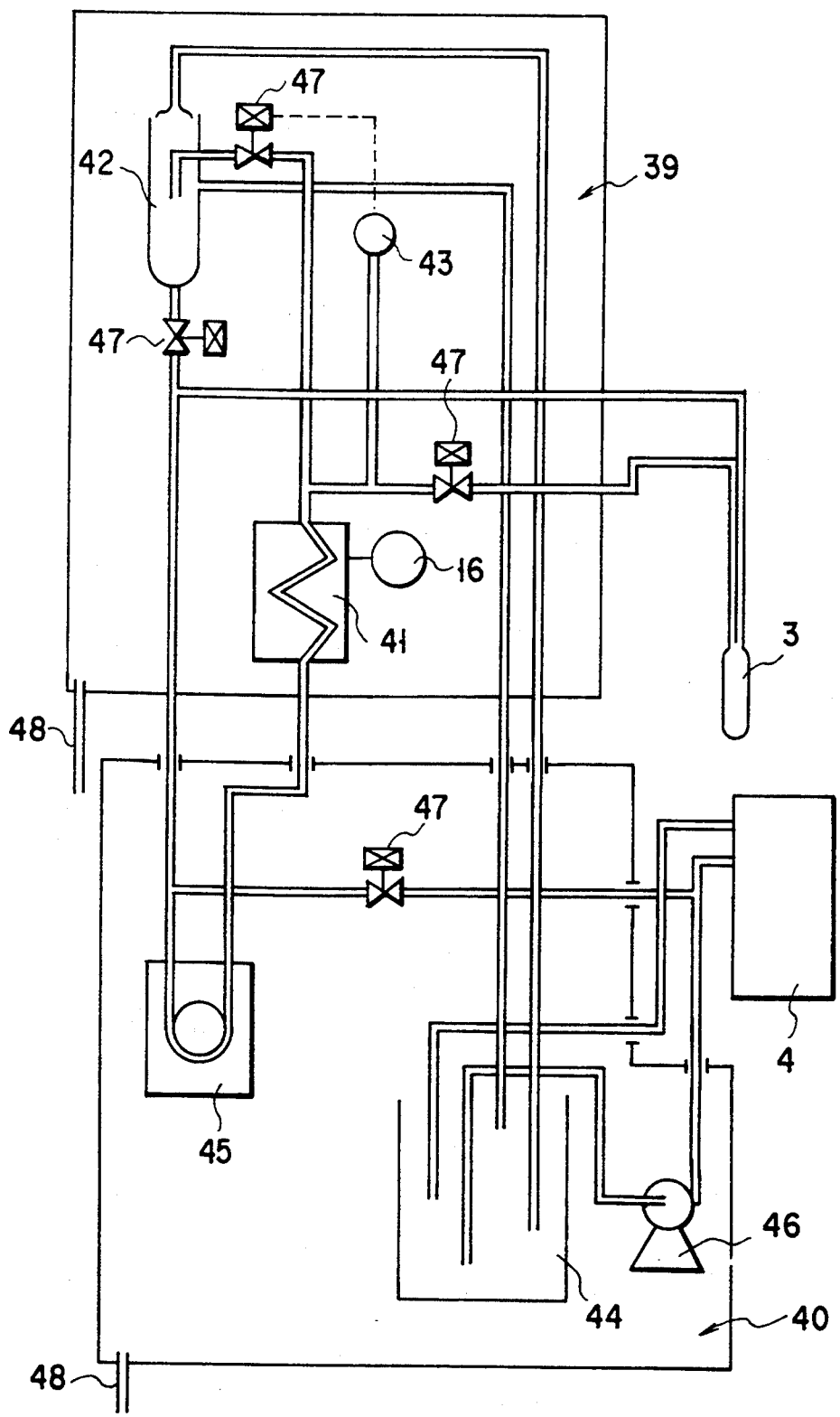
F I G. 5

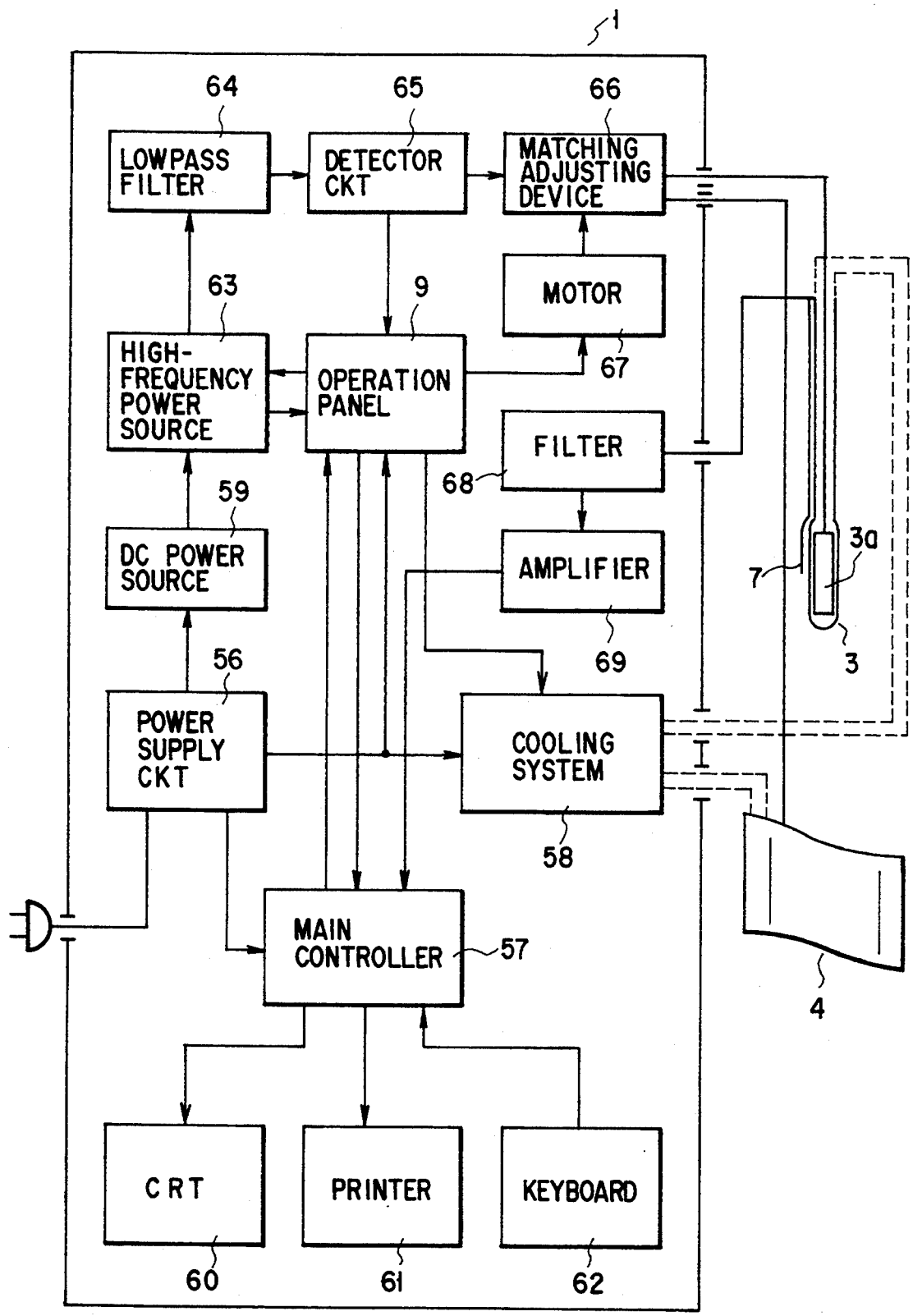
F I G. 8

```
** CONTROL PARAMETER **
```
| | | | |
|---|---|---|---|
| 77 — CONTROL | MODE | ☐ | AUTO |
| | SENSOR | : | MAX |
| 78 — RANGE | HIGH | : | 45.0 (°C) |
| | LOW | : | 40.0 (°C) |
| 79 — TIME | WAIT | : | 1 (min) |
| | HEAT | : | 30 (min) |
| | COOL | : | 3 (min) |
F I G. 10
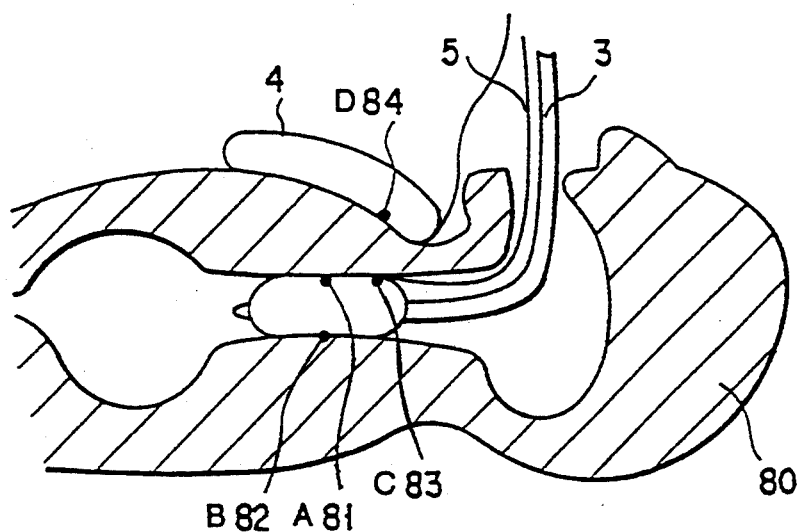
F I G. 11

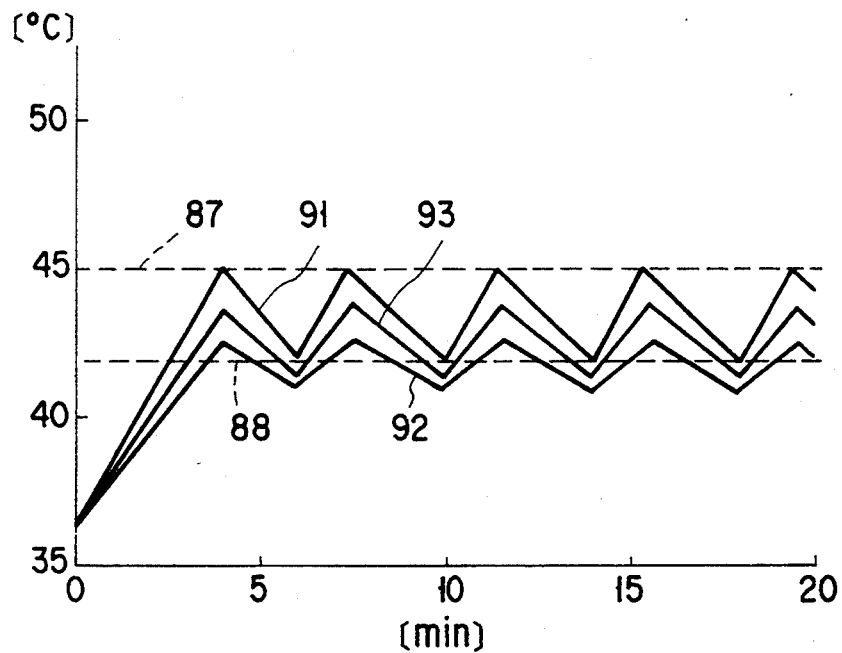
F I G. 17
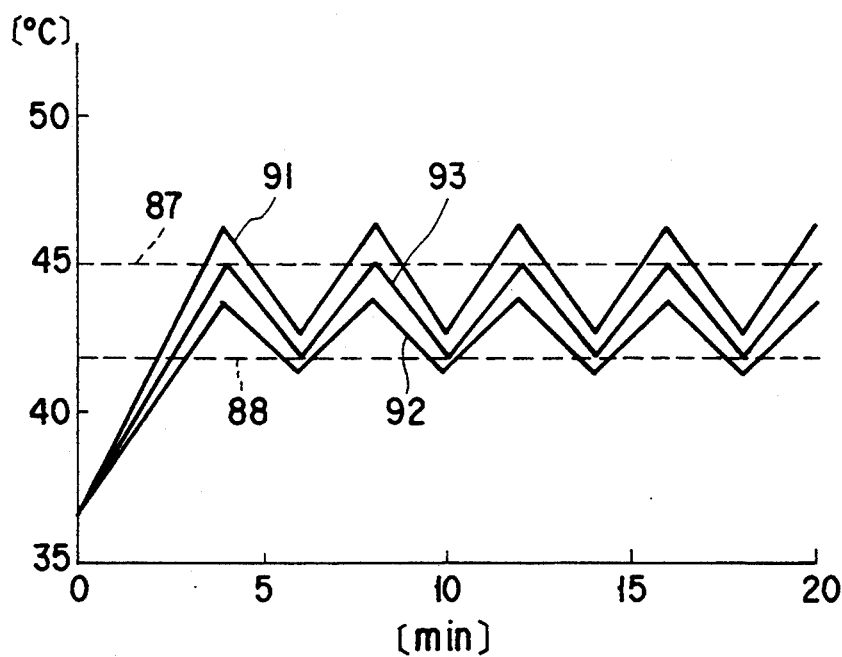
F I G. 18

METHOD AND APPARATUS FOR THERMOTHERAPY

This application is a continuation of application Ser. No. 07/845,625, filed Mar. 4, 1992, now abandoned.

BACKGROUND OF THE INVENTION

1. Field of the Invention

The present invention relates to a method and apparatus for thermotherapy which treats an affected region of a human being at an elevated temperature.

2. Description of the Related Art

Published Unexamined Japanese Patent Application Nos. 61-58671 and 61-58672 disclose a system for measuring temperature at a plurality of sites in a region of interest of a human being so that the region of the human being can be treated at an elevated temperature. The disclosed system is adapted to uniformly elevate temperature at the whole region of interest through the control of a temperature-elevating energy simply by providing an output corresponding to one of a plurality of measuring sites to be warmed. A result of temperature measurement at other sites is employed for a mere consideration or attention and is not used for the control of the temperature-elevating output. Through the measurement by the one and only temperature sensor at the region of interest, the temperature there can be controlled under the predetermined conditions until the medical treatment is complete.

The conventional treating apparatus of this type is adapted to, prior to starting a thermal treatment, select one of the temperature sensors and to control a temperature-elevating output, for the whole region of interest based on temperature data measured by the specific temperature sensor thus selected. However, there arises a problem as will be set out below.

In the conventional apparatus, prior to the start of medical treatment, one of the temperature sensors is selected for temperature control. Since the selected temperature sensor allows predetermined control only to an extent restricted by a result of its measurement, no optimal temperature can be obtained from that measurement as viewed from the region to be temperature-elevated. The temperature involved is sometimes increased too high at some part or decreased too low at other parts of the region of interest, thus sometimes failing to adequately and effectively treat the whole region of interest of the human being. A part of the body cavity region, if being locally temperature-raised too high, causes a local burn there, requiring a proper margin of safety. This also inhibits efficient medical treatment on the region of interest of the human being.

SUMMARY OF THE INVENTION

It is accordingly the object of the present invention to provide a method and apparatus for thermotherapy which can perform proper output control whereby it is possible to optimally treat an affected region of a human being in a proper temperature-elevated state in accordance with the situation under which it is treated.

According to the present invention there is provided an apparatus for thermotherapy which can treat an affected region of a human being at an elevated temperature, comprising:

means for elevating temperature at an affected region of the human being and for generating a temperature-elevating output in a variable fashion;

temperature measuring means, having a plurality of sensors, for individually detecting temperature at different sites in an area including the affected region of the human being;

means for selecting one or a plurality of temperature data signals of the respective sensors in accordance with each object with which the affected region is temperature-elevated and for generating a signal corresponding to the selected temperature data;

means for comparing the selected one temperature data signal or the plurality of temperature data signals with predetermined temperature range data and for generating a control signal for controlling a temperature-elevating signal; and control means for controlling the temperature-elevating output of the temperature-elevating means on the basis of the temperature-elevating signal and for setting the temperature at the affected region of the human being to be within the predetermined temperature range.

According to the present invention, optimal temperature control can be performed, thereby treating the affected region in a proper temperature-elevated state through the use of the temperature sensors for controlling an output in accordance with the treatment or through a proper combination of these temperature sensors. By so doing, it is possible to conduct an effective thermotherapy in an adequate temperature-elevated, but safe, range in accordance with the situation under which the affected region is located as well as the purpose for which a specific treatment is done.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a view showing an outer appearance of an apparatus for thermotherapy according to an embodiment of the present invention;

FIG. 2 is a front view showing an operation panel in the apparatus of FIG. 1;

FIG. 5 is an explanative view diagrammatically showing an arrangement for coolant circulation in the apparatus of FIG. 1;

FIG. 8 is an explanative view showing an arrangement of an electric circuit associated with a high-frequency oscillation/control system;

FIG. 10 is a view showing a CRT screen in the apparatus;

FIG. 11 is an explanative view showing a state in which applicators are employed in a body cavity for thermotherapy;

FIG. 17 is a view showing a temperature variation involved upon thermotherapy;

FIG. 18 is a view showing another temperature variation involved upon thermotherapy;

DETAILED DESCRIPTION OF THE PREFERRED EMBODIMENT

Figure 3:
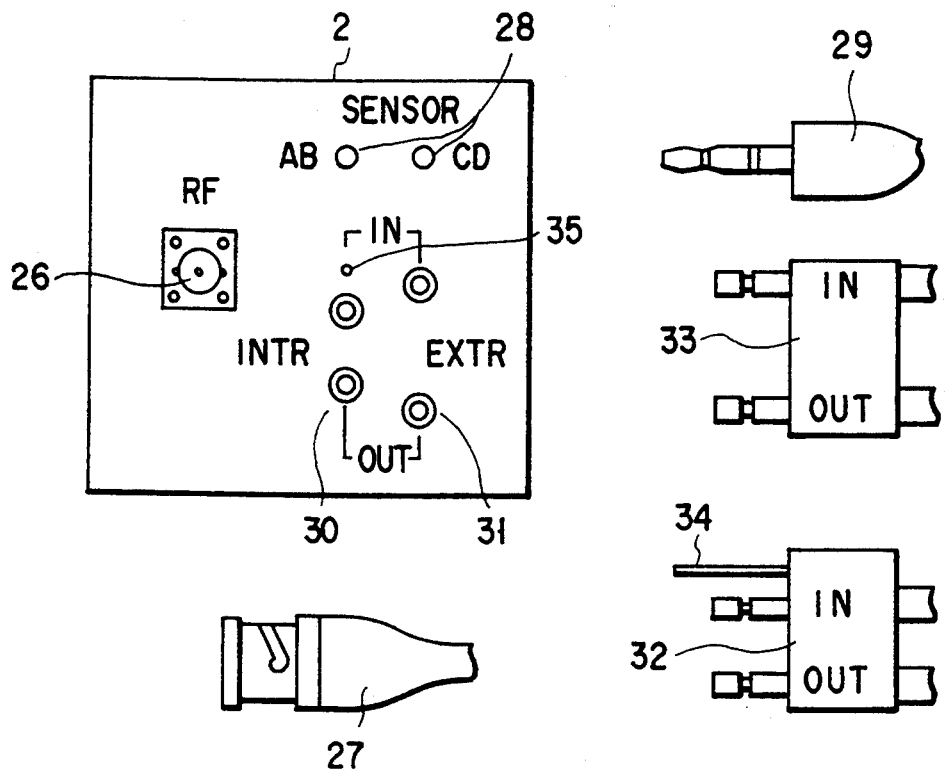
FIG. 3 is an explanative view showing an applicator box and associated connectors in the apparatus of FIG. 1.

A first embodiment of the present invention will be explained below with reference to the accompanying drawings.

FIG. 1 shows an outer appearance of an apparatus for thermotherapy having a body case 1. The body case 1 has an applicator box 2 which can be inserted into and withdrawn out of the body case 1. The applicator box 2 includes an internal applicator 3 for use in the cavity or tract of a human body, an external applicator 4 for use outside of the body, and a thermocouple 5 for use as a temperature sensor. The internal applicator 3 is of such a type as to be suitably used for the thermal treatment of the cavity organ, such as the esophagus, in particular. The internal applicator 3 has, at its tip portion, a built-in electrode 3a for a high-frequency (CF) wave as will be set out below.

An inflatable balloon 6 is provided on the tip end portion of the internal applicator at an area of the built-in electrode to allow circulation of a coolant through the inside of the balloon. The electrode is enclosed by the balloon. The balloon 6 can be inflated to have its outer peripheral surface brought into contact with the inner surface of the cavity. By so doing, it is possible to hold the applicator 3 in place in the body cavity. A tissue region of the body cavity near the outer peripheral surface of the balloon 6 is prevented from being burnt since the coolant is circulated through the inside of the balloon 6.

A plurality of temperature sensors 7, such as thermocouples, are provided on the outer peripheral surface of the balloon 6 and adapted to be set in contact with the body cavity of the human subject. It is to be noted that the thermocouples 5 are provided separate from the applicators 3 and 4 and can independently measure the temperature prevalent at desired sites, if necessary.

The external applicator 4 has a high-frequency (RF wave) electrode as a built-in electrode (external electrode) which is located in an opposed relation to the electrode of the internal applicator 3 with the living body interposed. A cooling passage is provided in the external applicator 4 at an outer area contacting with the body surface. When the external applicator 4 is mounted on the patient, the passage can cool the area so that he or she can be prevented from being burned there.

A cathode ray tube (CRT) 8 is provided at the upper section of the body case 1 so as to display the prevalent temperature, control information, etc., for thermal treatment. An operation panel 9 for controlling or adjusting the RF wave output, coolant circulation, etc., is located beneath CRT 8, followed by a computer 10 and a keyboard 11 downwardly. The keyboard 11 is used to enter, for example, data on the treatment of the patient. At the lowest section of the body case 1 are disposed, for example, a tank for storage of the coolant and a cooling system containing a storage chamber enclosing a pump for coolant circulation. Reference numeral 12 shows a storage door for the storage chamber.

The general arrangement and function of the operation panel 9 will be explained below with reference to FIG. 2.

The operation panel 9 is broadly divided into functional operation units, that is, a cooling unit 13 for the cooling system, a matching unit 14 for coordination and a power unit 15 for a high-frequency oscillation system, as will be set out below with reference to FIG. 2.

The cooling unit 13 includes an adjusting meter 16 for adjusting the temperature of the coolant through the internal applicator 3. A coolant as set at 42° C. by the coolant temperature adjusting meter 16 is circulated through the internal applicator 3. Further, a water pressure meter 17 is provided to detect the pressure of the coolant provided to detect the pressure of the coolant through the internal applicator 3 and is adapted to adjust a flow of a coolant through a circulation pump, not shown, in accordance with a coolant pressure level. The water pressure level is displayed on the water pressure meter 17. The pressure detection system serves to adjust the coolant pressure in a state of the accurate intimate contact of the applicator's balloon 6 with the cavity wall and to detect leakage of the coolant. The pressure detecting system adjusts an amount of coolant through the coolant circulation pump so that the coolant circulation pressure may be made at about 1000 mm H₂O, for example, in the treatment of the esophagus. A pump drive switch 18 is provided below the water pressure meter 17 to control the coolant circulation in an ON/OFF fashion. The pump drive switch 18 can control the driving of the pump for internal and external circulations of the coolant. A coolant passage selector 19 is provided below the coolant temperature adjusting meter 16. The selector 19 is comprised of a switching knob for selecting the coolant passage in the device in a corresponding mode of the coolant system with the use of an electromagnetic valve.

The matching unit 14 has a high-frequency reflectometer 20 and a matching control switch 21. The reflectometer 20 detects an RF wave reflected from the applicator side to an oscillator side via the applicator during the thermal treatment by the RF wave of a region of interest and displays that state as a reflectivity. Since a greater reflectivity leads to a poor performance of the oscillator, an alarm sound is generated, for example, when the reflectivity exceeds 10%. At this time, an alarm lamp is lit to inform the operator of the abnormal state of the reflectivity. The matching control switch 21 adjusts a matching control circuit in the applicator box 2, thus obtaining a better matching state between the applicators.

A power unit 15 includes a high-frequency output meter 23 and an output control knob 24. Switches 25 are provided to the right of the output control knob 24 to allow the starting/stopping of the high-frequency output and inputting of control items, etc. The switching of an automatic or a manual output control, etc., is performed by the switch.

The arrangement of the applicator box 2 will be explained below.

As shown in FIG. 3, the applicators 3 and 4, coolant tube, temperature sensor, etc., are connected at the front face side of the applicator box 2. The internal and external applicators 3 and 4 are connected via a BNC type connector 27 to a high-frequency (RF wave) output terminal 26. The temperature sensors have two connection sections 28, comprised of what is called "a stereojack", one connected to a sensor AB side and the other connected to a sensor CD side. For example, the temperature sensor 7 mounted on the internal applicator 3 is connected to the sensor AB side and a temperature sensor is connected as a single unit to the sensor CD side. The connection of these temperature sensors is achieved by the insertion of a stereopin type plug 29.

At the applicator box 2, a connector 30 for the internal applicator 3 is provided for the connection of a coolant tube and a connector 31 for the external applicator 4 is provided for the same purpose. A connector 32 for an internal coolant tube is connected to the connector 30 and a connector 33 for an external coolant tube is connected to the connector 31.

Here since, depending upon the flow direction of a coolant, air in the internal applicator 3 varies in the readiness with which it is drawn, a pin 34 and hole 35 are provided at the connector 32 and application box 2, respectively, so that the connector 32 is not connected in a reverse fashion. Thus the pin 34, being insertable into the hole 35, is connected to the connector 32. For this reason, the coolant tube can exactly be connected to the internal applicator 3, thus failing to make any connection error with the directions IN and OUT set the other way around.

Figure 4:
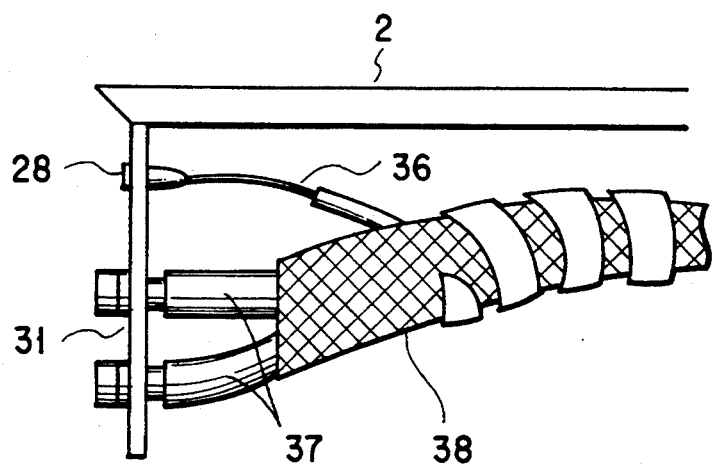
FIG. 4 is an explanative view showing a part of the application box in the apparatus.

FIG. 4 shows a part of the inside of the applicator box 2. A compensation conductor 36 and coolant tubes 37 for the temperature sensor are bundled in the applicator box 2 and, with the bundled state, connected to the body case 1 side. Since a coolant of, for example, about 40° C. is circulated through the coolant tube 37, if the coolant tubes 37 and compensation conductor 36 are simply bundled together, the compensation conductor 36 is adversely affected by heat, causing a temperature error. In order to prevent a temperature error, the compensation conductor 36 and coolant tubes 37 are bundled together with a heat insulating material 38 interposed between the compensation conductor 36 and the coolant tube 37. By so doing, the compensation conductor 36 is not adversely affected by the temperature of the coolant, suppressing the generation of a temperature error.

FIG. 5 diagrammatically shows a pipe arrangement of the cooling system in the body case. The cooling system is broadly classified into two units, that is, a first cooling unit 39 located in the upper zone of the body case 1 and a second cooling unit 40.

The first cooling unit 39 primarily supplies the coolant to the internal applicator 3 for circulation. The cooling system in the cooling unit 39 includes a heater 41 for heating coolant temperature at a constant level and a cooling pot 42 provided for removing a gas in the internal pipe for the body cavity, keeping an amount of coolant at a constant level, etc. In order to control the coolant temperature at a maximal temperature, the heater 41 has its output controlled through the temperature regulator set out below. The temperature regulator 16 may control the coolant at a proper level in accordance with temperature measuring data of a temperature sensor as will be set out below which detects the temperature of a region of interest of a patient or the temperature of the internal applicator 3. A pressure detector 43 is provided in the internal cooling pipe to detect the pressure of the coolant circulated in the internal applicator 3.

The second cooling unit 40 includes a coolant tank 44 for holding a coolant, an internal pump (for body cavity) 45 comprised of a rotary pump for the circulation of the coolant through the internal applicator 3 and an external pump (for outside use) 46 comprised of an electromagnetic pump for the circulation of the coolant through the external applicator 4.

The internal pump 45 uses a roller pump, thus enabling, to be controlled, a flow of the coolant which is circulated through the internal applicator 3. The external pump 46 is of an electromagnetic type with a flow of the coolant fixed. The electromagnetic pump 46 flows more coolant than the roller pump and serves the purpose when simply more area is to be cooled. The external pump 46 allows the coolant in the coolant tank 44 to be circulated through the external applicator 4.

An electromagnetic valve 47 is provided in each of these cooling systems 39 and 40. These electromagnetic valves 47 are switched by the cooling path selector 19 on the operation panel 9, thereby enabling the injection of the coolant into the internal applicator 3, aspiration of air, discharge of water, etc.

A drain tube 48 is arranged at the first and second cooling units 39 and 40. Even if the coolant should leak from the cooling system, it is discharged out of the apparatus via the tube 48, preventing the water from splashing on those circuit component parts in the electric system.

The detector 43 for detecting the pressure of the coolant in the internal applicator 3 will be explained below with reference to FIG. 6.

The pressure detector 43 has a piezoelectric element 50 on the bottom of a container communicating with the coolant passage in the internal applicator and detects a pressure prevalent in the container 49 as an electrical signal through the pressure/signal conversion by the piezoelectric element 50. The pressure in the container is detected as the prevalent coolant pressure and hence as a corresponding electrical signal. The output of the piezoelectric element 50 is transmitted to a pressure detection circuit through lead wires 51. The container 49 has two tube connection sections, one being a connector 53 for connection by a tube 52 for pressure detection which communicates with a coolant passage for circulating the coolant and the other being a connector 55 for aspirating air in the container 49. To the connector 55 is connected a tube 54 for controlling an amount of air in the container 49.

The container 49 in the pressure detector 43 is held hermetically air-tight by introducing a coolant into the container 43 via the connector 53 and closing the tube 54 when the coolant in the container 49 reaches a given level. The pressure of the coolant flowed into and out of the container 49 is detected in the state as set out above. At that time, the height level at which the pressure detector 43 is situated is desirably set at the height level of the patient where the internal applicator 3 is positioned at a time of medical treatment. Taking the height of the bed for treatment into consideration, the pressure detector 43 in the apparatus is positioned at a height of, for example, about 80 cm.

Why the pressure in the container 49 is detected in a water/coolant mixed state will be explained below.

A roller pump is employed as the internal pump 45 for circulating the coolant toward the internal applicator 3 side. If the roller pump is used, a pulsating flow occurs in the coolant flow when the coolant is sent out of the roller pump. Upon the direct measurement of that pressure, the needle of the pressure meter 17 is disturbed due to that pulsating flow. In order to avoid such a phenomenon, air is utilized as a damper so as to reduce the pulsating motion in the pressure detector 43. That is, the vibration of the pressure meter 17 can be reduced through the utilization of the air as the damper.

Figure 6:
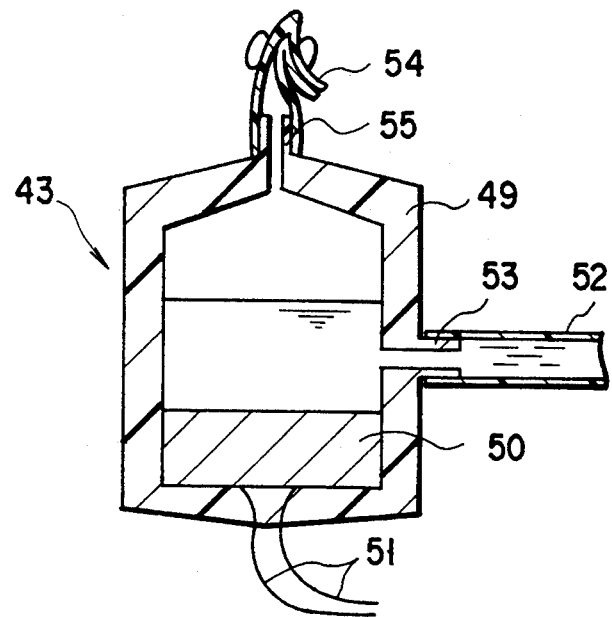
FIG. 6 is a cross-sectional view showing a pressure detector in the apparatus.
Figure 7:
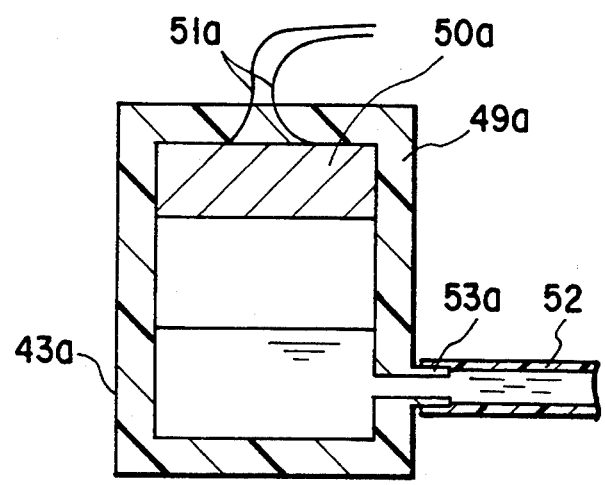
FIG. 7 is a cross-sectional view showing another form of a pressure detector in the apparatus.

A pressure detector 43a as shown in FIG. 7, though being somewhat different from the pressure detector 43 as shown in FIG. 6, serves the same purpose as that of the pressure detector 43. In the pressure detector 43a, a piezoelectric element 50a is provided at the uppermost zone in a container 49a and air pressure in the container 49a acts upon the piezoelectric element 50a. An air vent is not provided in the container 49a of the pressure detector 43a. Even the pressure detector 43a, like the aforementioned pressure detector 43, can detect pressure under a situation in which the vibration is reduced.

The arrangement of an electrical system in the apparatus for thermotherapy will be explained below with reference to FIG. 8.

In the body case 1, a power supply circuit 56 supplies power to a main controller 57, cooling system 58 and DC power supply 59. The main controller 57 performs major control of the electrical system in the body case 1, such as temperature measuring control, display of a controlled state, printer control and keeping of patient data. A CRT 50, printer 61 and keyboard 62 are connected to the main controller 57. CRT 60 displays a temperature-measured state, controlled state, etc. Under the control of the main controller 57, the printer 61 can print temperature-raising data upon thermotherapy. The keyboard 62 is used to enter, for example, patient's data.

The cooling system 58 is controlled by the operation of the operation panel 9 and enables a coolant to independently circulate through the internal and external applicators 3 and 4. The arrangement of the cooling system is as set out above with reference to FIG. 5. The coolant may be shared between the internal and external applicators 3 and 4.

The DC power supply 59 is comprised of a power source for driving a high-frequency power source 63 for oscillating a high frequency wave (RF wave). The high-frequency power source 63 is controlled by the operation panel 9 and the output of the high-frequency power source 63 is controlled in an ON/OFF fashion. The output of the high-frequency power source 63 may be variably controlled in a continuous fashion. The RF wave which is oscillated at the high-frequency power source 63 has its noise of over 13.56 MHz eliminated past a lowpass filter 64. The 13.56 MHz RF wave is transmitted to a detector circuit 65. The output of the detector circuit 65 is adjusted by a matching adjusting device 66 in its matched state and the outputs of the matching adjusting device are supplied to the internal and external applicators 3 and 4. The matching adjusting device 66 has a variable capacitor which is adjusted by a motor 67 to obtain a better matched state.

The detector circuit 65 detects both a travelling wave and reflected wave resulting from the high-frequency wave and electric power thus detected is displayed on a corresponding meter on the operation panel 9. The matched state is so adjusted that the reflectivity is brought to zero while looking at a "reflectivity" needle on the display.

For the measurement of temperature, a temperature signal coming from the temperature sensor 7, or the other temperature sensor or sensors, at the internal applicator 3 is supplied through a filter 68 to an amplifier 69 where it is amplified. The amplified output is delivered to the main controller 57. The temperature sensor 7 is subject, by the high frequency wave, to an influence resulting from a noise to produce a temperature error. The filter 68 is provided for this purpose, that is, to mainly eliminate the noise resulting from the high-frequency wave. The temperature signal which comes from the amplifier 69 is, for example, graphically shown on the display screen of CRT 60.

In order to maintain temperature prevalent at the region of interest of the patient constant, the high-frequency output is controlled by the temperature signal in the ON-OFF fashion. The ON/OFF signal of the oscillated high-frequency wave, after being compared with a set temperature-elevating level, is supplied to a control unit on the operation panel 9. The control unit on the operation panel 9 turns the high-frequency power source 63 ON and OFF.

Figure 9:
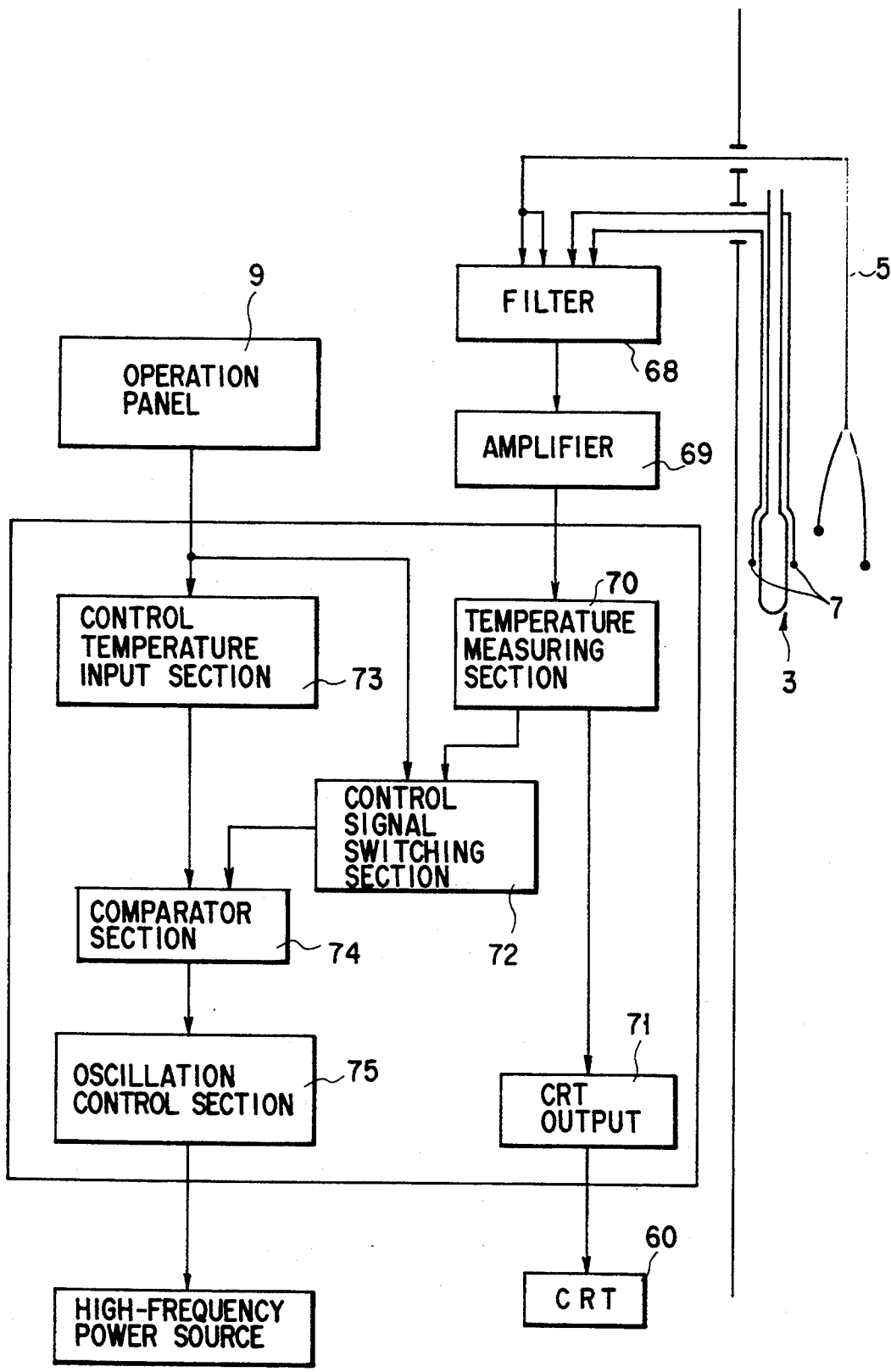
FIG. 9 is an explanative view showing, in a block array, an arrangement of a temperature measuring-/high-frequency output control system in the apparatus.

The temperature measuring and high-frequency output controls will be explained in more detail below with reference to a block diagram in FIG. 9.

The temperature signal which is amplified by an amplifier 69 is supplied to a temperature measuring section 70 where the temperature signals of the respective sensors (for example, A, B, C and D) are converted to temperature data. The output of the temperature measuring section 70 is delivered to a CRT output section 71 and control signal switching section 72. The CRT output section 71 performs signal processing for displaying a temperature graph relating to a real-time temperature involved and sequentially varying time on the CRT screen. The high-frequency output control mode (manual or automatic), temperature sensor select input information, temperature control range, temperature-elevating time, etc., are entered from the operation panel 9. These entered information items are supplied to a control temperature input section 73 and control signal switching section 72. As data for setting a control temperature range, for example, a maximal temperature of 45° C. and minimal temperature of 40° C. are entered as data to the control temperature input section 73.

A select signal, that is, a signal for selecting a temperature sensor serving as a temperature control reference, is input to the control signal switching section 72. Let it be assumed that there are four sensors A, B, C and D. In this case, two methods can be used to select the temperature sensor for temperature control reference, one selecting one of the temperature sensors A to D and the other selecting two or more of the temperature sensors A to D so as to control an output by a higher one of these temperature sensors.

The temperature sensor temperature data required is supplied to a comparator section 74 in accordance with the operation of the temperature sensor selecting means. The comparator section 74 compares the maximum and minimum temperatures of the set temperature control range with the temperature data of the temperature sensor selected and delivers a result of comparison, as a temperature control signal, to an oscillation control unit 75. The oscillation control unit 75 is of such a type that, depending upon the result of comparison, it delivers an OFF control signal when the temperature involved exceeds the control temperature and an ON control signal when the temperature involved is below the control temperature. In this case, the OFF and ON control signals are employed to turn the high frequency power source OFF and ON.

As set out above, it is possible to enter data relating to the RF control mode, reference temperature sensor for control, temperature control range, temperature elevating time, etc., prior to the start of the medical treatment and, even if upon therapy (upon RF oscillation), to perform temperature resetting after the output has been temporarily interrupted.

FIG. 10 shows the contents of a set image screen 76 on CRT 8 when the aforementioned conditions are set. The contents of the set image screen are broadly classified into three items: the first item (CONTROL 77) relating to the high frequency (RF) control method, the second item (RANGE 78) relating to the temperature control range for high-frequency ON/OFF outputs, and the third item (TIME 79) relating to a control time from the start of the medical treatment to its end.

The item "MODE" in CONTROL 77 shows an automatic control mode (AUTO) to be done in a temperature range for setting the ON/OFF control of the high-frequency output and a high-frequency output ON/OFF mode (MAN) to be manually done while viewing the temperature on the image screen of CRT 8 without considering the temperature range at all. "SENSOR" in the item "CONTROL 77" selects the temperature sensor for temperature control reference. The temperature not selected is displayed on the image screen of CRT 8 for attention only. The sensors A, B, C and D are selected by the two methods: one method being used to select one of the sensor A, B, C or D and the other method being used to select the sensors A, B, C and D in a combination of AB, AC, AD, BC, BD, CD, ABC, ABD, ACD, BCD and MAX (ABCD). In the case where the plurality of sensors are selected, the high-frequency output is controlled in the ON/OFF fashion by the output of the sensor corresponding to the highest temperature detected.

The item "RANGE 78" shows two items "HIGH" and "LOW" which are effectively employed for automatic control. The item "HIGH" is used to set the high-frequency output at an OFF level when the output of the temperature sensor serving as a reference exceeds the set level. On the other hand, the item "LOW" is used to set the high-output at an ON level when the temperature of the above-mentioned reference temperature sensor is declined below the set level. The high-frequency output is controlled by the automatic control so that the temperature of the reference temperature sensor is maintained at a "HIGH" or a "LOW" temperature range.

The item "TIME 79" shows three modes "WAIT", "HEAT" and "COOL". The mode "WAIT" sets a time for starting the temperature measuring for medical treatment and displays a corresponding temperature on the form of a graph on the CRT screen but, in the "WAIT" state, the high-frequency wave is not produced as an output and hence the temperature rise is not started. The mode "HEAT" is used to set a time from a start to an end of elevating temperature after the high-frequency wave is produced. In this case, the temperature elevating time is not started at a time when the high-frequency wave is output, and it is not until the output of the reference temperature sensor just falls in the temperature control range after the high-frequency wave has been output that the count is started. The mode "COOL" sets a time just after the temperature rise resulting from the outputting of the high-frequency wave has been completed. By so doing, the temperature of a region of interest (ROI) of the patient can be so cooled that the ROI is brought to substantially the same temperature as the body temperature of the patient.

FIG. 11 shows the state in which the internal and external applicators 3 and 4 are attached to the patient for thermotherapy. As shown in FIG. 11, the internal applicator 3 is inserted into a cavity organ, such as the esophagus, with the external applicator 4 mounted on the body surface of the patient in an opposed relation to the internal applicator 3. By so doing, the ROI is sandwiched between the internal and external applicators and, in this state, a high-frequency wave is applied to the ROI of the patient. The temperature there is measured by the sensors A81, B82 on the internal applicator 3 as well as the sensors C83, D84 formed of a single unit.

Figure 12:
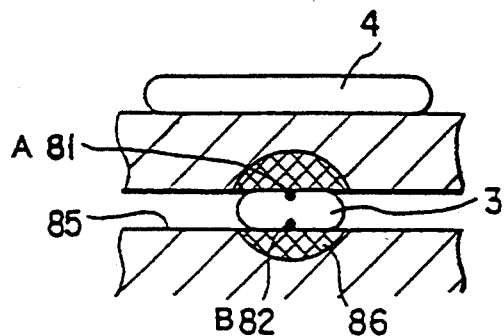
FIG. 12 is an explanative view showing the applicators attached to a patient for thermotherapy to be done in a body cavity of a patient.

The selection of which sensors should be selected upon thermotherapy on the ROI of the patient will be explained below in more detail by way of example. FIG. 12 shows the case where an affected region (ROI) 86 on the cavity organ 85 of the patient is thermally treated at which time the temperature there is elevated through an internal applicator 3 as well as an external applicator 4 of such a type as to be wrapped partway around the patient body. In this case, the external applicator 4 of such type is oriented only in one direction to the internal applicator 3 and the temperature sensor A81 side of the internal applicator 3 is normally heated to the highest extent. If there is a risk of a burn on the ROI of the patient upon thermotherapy, the temperature sensor A81 is selected as the reference temperature sensor. That temperature data is compared with the set data to produce a determination signal based on a result of comparison. It is, therefore, possible to control an output corresponding to a heating energy by these applicators 3 and 4. It is to be noted that the temperature data as obtained at the temperature sensor B82 can be employed simply as an attention temperature.

Even if the method for medical treatment as shown in FIG. 12 is utilized, there are sometimes the cases where the temperature at the sensor A81 and that at the sensor B82 are reversed relative to each other depending upon the extent of attachment of the internal applicator 3, the manner of the coolant circulated through the internal applicator 3, and so on. For a medical treatment to need to be done in a manner to completely prevent a burn on the inner wall, temperature control has to be effected by selecting both the sensors A and B as the reference temperature sensors and to be so done without involving such a burn on the inner wall anywhere around the internal applicator 3.

If a medical treatment is to be effected, for example, based on a concept that an affected region of the patient has to be treated at an elevated temperature of over 43° C. at min. and that some burn is unavoidable as the case may be, then a method may be adopted by which a minimum temperature is secured relative to the affected region 86 while selecting the sensor B82 as the reference temperature sensor.

Figure 13:
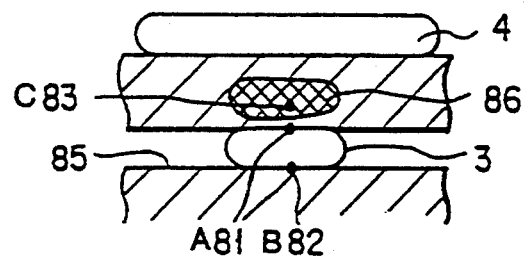
FIG. 13 is an explanative view showing the applicators attached to a patient for thermotherapy to be done in a body cavity of a patient.

FIG. 13 shows a state in which an affected region 86 is present in the inner wall of a cavity organ 58. In this case, the sensor C83 is inserted into the affected region 86 of the patient and temperature control can be done with the temperature sensor C83 as the reference temperature sensor. By so doing, medical treatment can be done at an elevated temperature which is a temperature necessary for the affected region 86. The temperature detected at the temperature sensors A and B is utilized for attention only. In this situation, care has to be exercised not to burn a normal tissue at the cavity wall of the patient. It is possible to control the temperature of the coolant through the internal applicator 3, or an amount of water involved, so that any burn may not occur in the normal tissue. In the case where any burn should be avoided at any cost, temperature control can be effected by selecting the other temperature sensors A81, B82 and C83.

Figure 14:
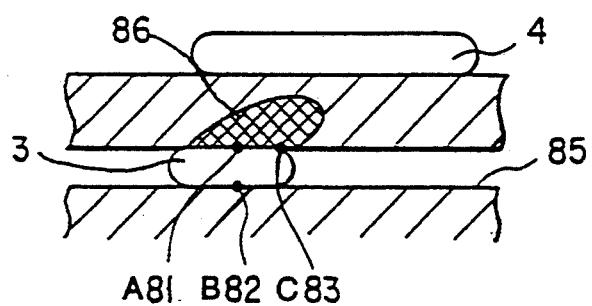
FIG. 14 is an explanative view showing the applicators attached to a patient at an affected region offset in a direction of his or her body cavity.

FIG. 14 shows a state in which an affected region 86 is offset in its progressing direction, not simply situated in its depth direction. For the treatment of such affected region 86, not only the internal and external applicators 3 and 4 are attached in an opposed relation to the affected region but also the external applicator 4 is positioned in a manner rather offset in the progressing direction of the affected region. Although the internal applicator 3 has the sensor A81 on the external applicator 4 side, it may be said that this sensor is not optimally positioned as the sensor for the treatment of the affected region 86 because it is situated at the center of the electrode on the internal applicator 3.

Therefore, the sensor C83 is positioned in the progressing direction of the affected region 86 so that it is used as the reference sensor. Temperature control can also be done by selecting the sensors A81 and C83 and using their outputs. It is possible to perform substantially optimal temperature control even in the case where an affected region of the patient is offset in its progressing direction.

Figure 15:
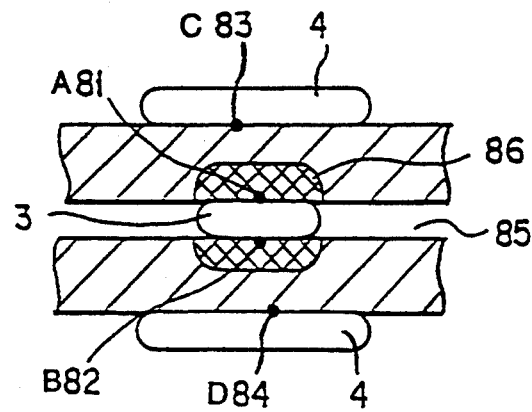
FIG. 15 is an explanative view showing the applicators attached to a patient at an affected region involved around his or her body cavity.

FIG. 15 shows a state in which, in order to medically treat an affected region 86 developed around the full circumferential inner wall portion of the body cavity of a patient, the inner applicator 3 is inserted into the body cavity so that it is located in a proper position with the external applicator 4 wrapped around the corresponding full circumferential body portion of the patient.

In this case, since the affected region 86 is situated around the full circumferential inner wall portion of the body cavity, the sensors A81 and B82 are selected as the reference temperature sensor and temperature control is achieved by the outputs of the sensors A81 and B82. The sensors C83 and D84 are employed to display the outside temperature for attention only. In the case where there exists any local area outside the body where a high-frequency current is liable to be concentrated due to an inadequate attachment of the external applicator to the outside skin of the patient, the sensor C83 or the sensor D84 is attached to the local area and, in this case, the temperature sensors A81, B82, C83 and D84 (MAX) are employed as the reference temperature sensors, thus preventing a burn on the external applicator 4 side.

The state of a variation at a temperature elevated by a high-frequency wave in actual practice will be explained below with reference to the drawing. An explanation will be given below about, for example, the case where the internal applicator 3 is attached as shown in FIG. 4 with the temperature sensors A81, B82 and C83 positioned as indicated. In this case it is to be noted that the external applicator 4 is placed on a lower side as viewed in FIG. 16.

FIG. 17 is a graph showing a temperature variation when the sensor A81 is employed as the reference temperature sensor, noting that the hour [min.] and temperature [°C.] are plotted as the abscissa and ordinate, respectively. In the graphical representation, the lines are plotted as a temperature control range where the upper and lower limits are denoted by 45° C. and 42° C., respectively. The temperatures of the sensors A81, B82 and C83 are represented by the lines A, B and C, respectively, in a graph of FIG. 17.

Figure 16:
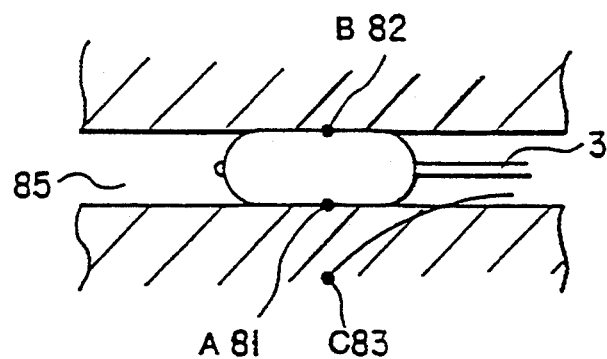
FIG. 16 is an explanative view showing one of the applicators which is attached to a patient with a plurality of temperature sensors positioned relative to his or her body cavity for thermotherapy.

Upon thermotherapy using a method shown in FIG. 16, the sensors A81 and B82 are temperature-elevated in that order. When, in this case, temperature control is conducted with the sensor A81, the oscillation of a high-frequency wave is controlled within a temperature range controlled with the sensor A81 whereas temperature at other sites (sensors B82 and C83) is set to be somewhat lower than the controlled temperature range.

When the output control is conducted, as shown in FIG. 18, with the temperature sensor C82 as the reference temperature sensor, the temperature at the sensor A81 will exceed that controlled temperature range. It is to be noted that this type of temperature-elevating method is necessary in the case where the temperature raised is set at the area 81.

Figure 19:
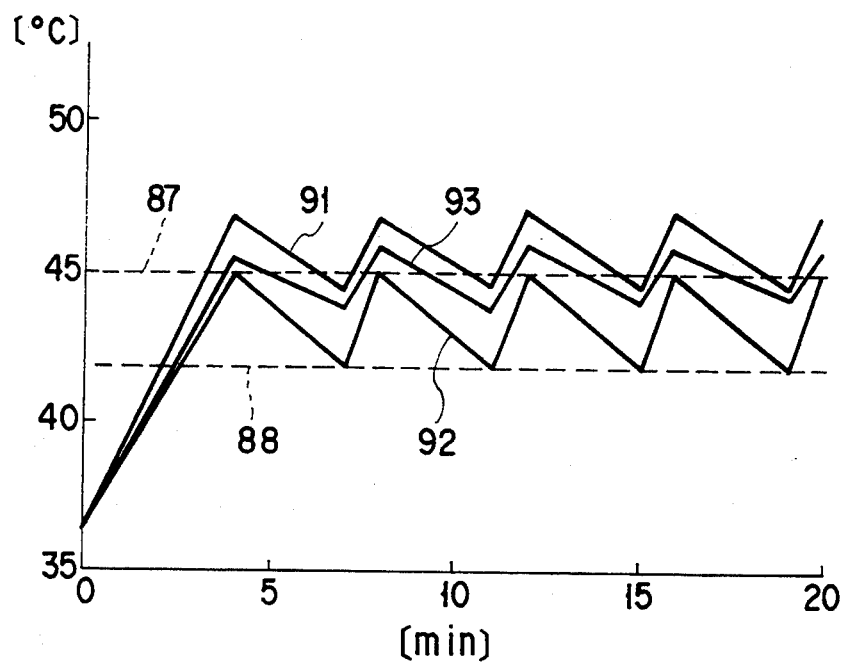
FIG. 19 is a view showing another temperature variation involved upon thermotherapy.

FIG. 19 is a graph plotted when the temperature sensor B82 is selected as the reference temperature sensor. In this case, this type of temperature-elevating method is required when the temperature is set to a minimal requisite level. This is done, though the temperature at other sensors exceeds a control range.

Figure 20:
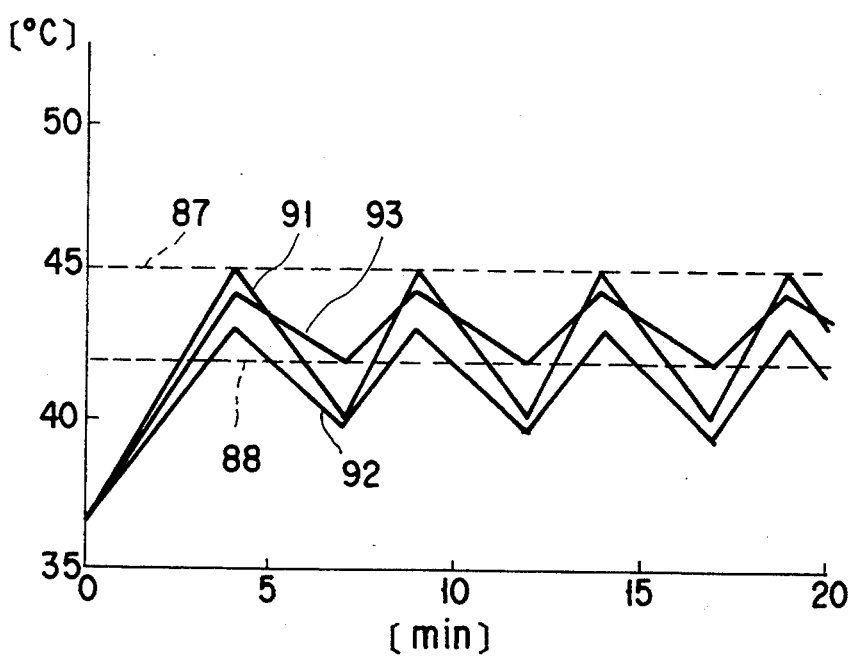
FIG. 20 is a view showing another temperature variation upon thermotherapy.

FIG. 20 shows the case where the temperature sensors A81, B82 and C83 are all set as the reference sensors. What is shown in FIG. 20 corresponds to, for example, the case where heat is difficult to dissipate in a tissue lying around the sensor C83. In this situation, the upper limit shows the level at which the output of the high-frequency wave is stopped with the use of the sensor A81 whereas the lower limit shows the level at which the high-frequency wave is output with the use of the sensor C82.

A second embodiment of the present invention will be explained below with reference to FIGS. 21 to 24.

The second embodiment of the present invention is similar in its basic arrangement and function to the first embodiment of the present invention. The second embodiment uses a method for adjusting the level of the output of a high-frequency power source, not the method for controlling the output of the high-frequency power source in an ON/OFF fashion. This type of system adjusts the output level of the high-frequency power source so that the temperature prevalent at an affected region of the living body is controlled in a predetermined range.

Figure 21:
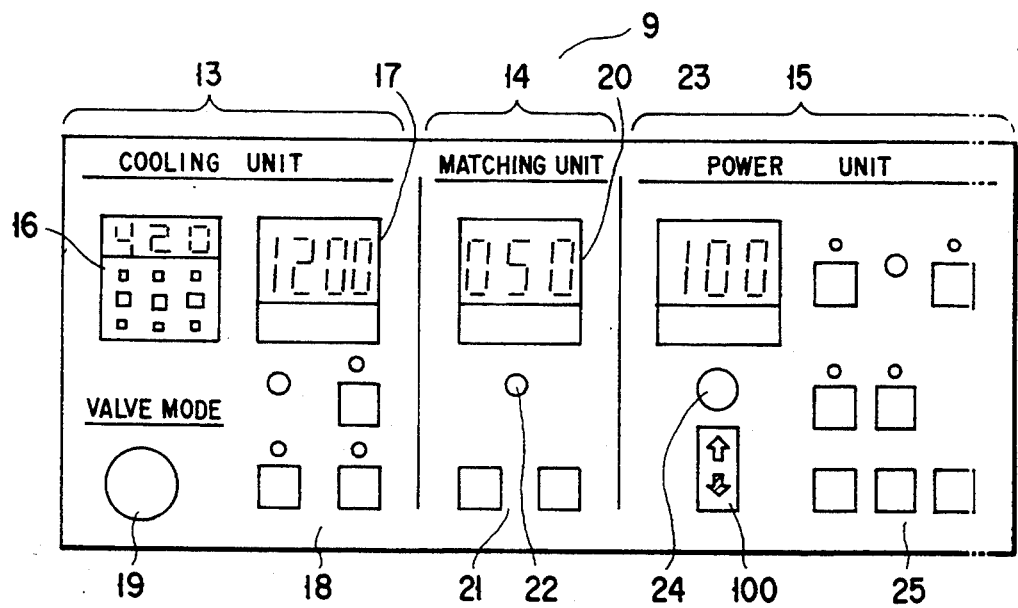
FIG. 21 shows an output display on an operation panel in a second embodiment of the present invention.

Here, since the output of the high-frequency power source is adjusted, as shown in FIG. 21, a corresponding output level can be traced, as a digital representation, on an output display 23 of an operation panel 9. The corresponding digital data can also be displayed on a reflectivity display 20 and on a coolant display. Further, the increase or decrease of the output level is displayed by corresponding arrows on a lamp display 100 at a left lower section of a power unit 15.

Figure 22:
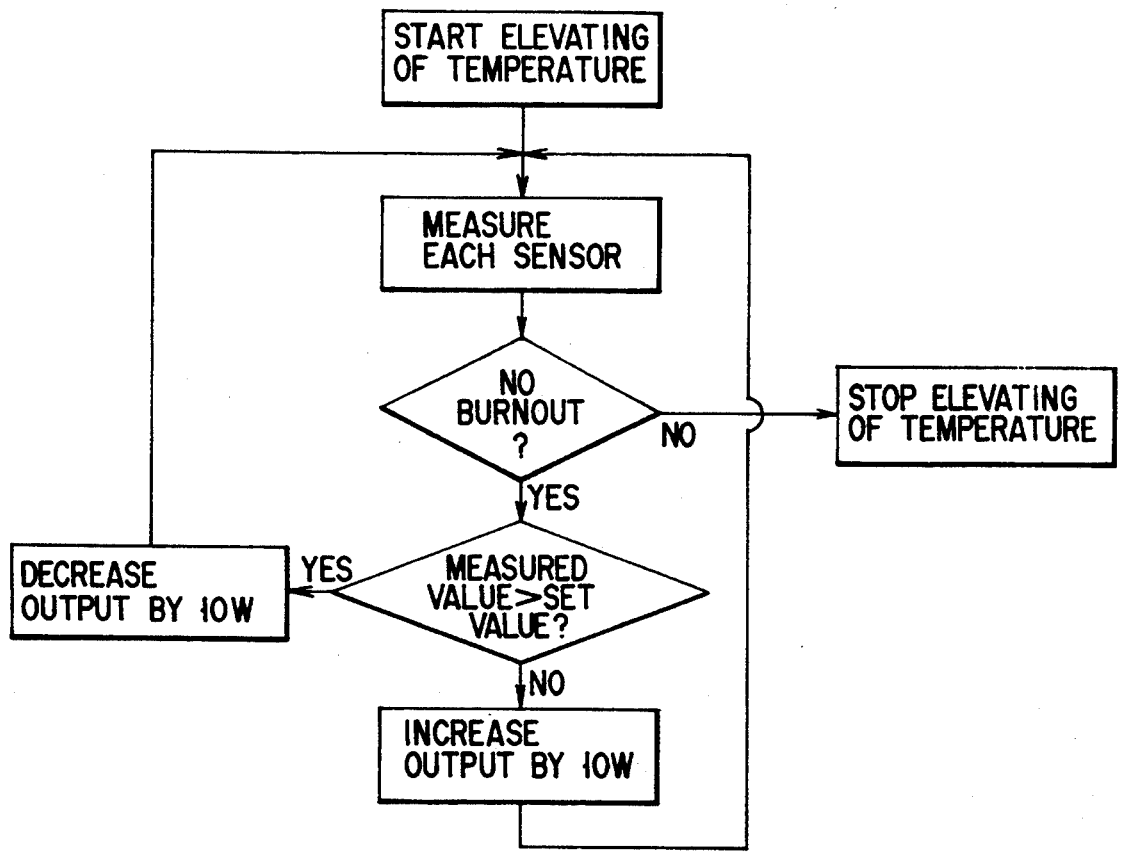
FIG. 22 is a flow chart on the elevating of temperature as achieved in the embodiment of FIG. 21.

FIG. 22 shows a flow chart on the elevating of temperature by a main controller 57. After a temperature increase is started, temperature measurement is conducted by the respective temperature sensors involved. Checking is made to see whether or not there occurs a burnout. In the case where, for example, a thermocouple is used as the temperature sensor, a burnout is checked when a corresponding electromotive force is not produced. A temperature-elevating operation is stopped promptly when one element of the thermocouple now in use is broken.

In the case where there is no burnout in the thermocouple elements, a maximal one of those measured values detected by a selected one or more temperature sensors is compared with an initially set temperature-elevating value. When the measured value is greater than the set temperature-elevating value, the present output of the high-frequency power source is taken as a value minus 10W. At the same time, a downwardly oriented arrow appears bright on a lamp display 100. When, on the other hand, the measured value is smaller than the set temperature-elevating value, the output of the present high-frequency power source emerges as a value plus 10W. At the same time, an upwardly oriented arrow appears bright on the lamp display 100. A series of temperature control continues until the elevating of the temperature is completed. The output value of the high-frequency power source may be controlled in an analog (continuous) fashion without increasing or decreasing the output of the high-frequency power source in a given rate.

Figure 23:
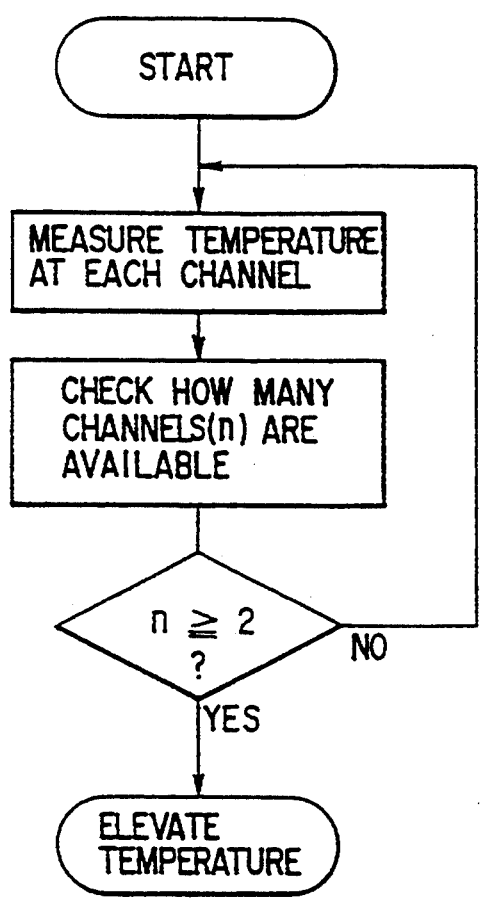
FIG. 23 is a flow chart for checking the operation of respective sensors prior to the elevating of the temperature.
Figure 24:
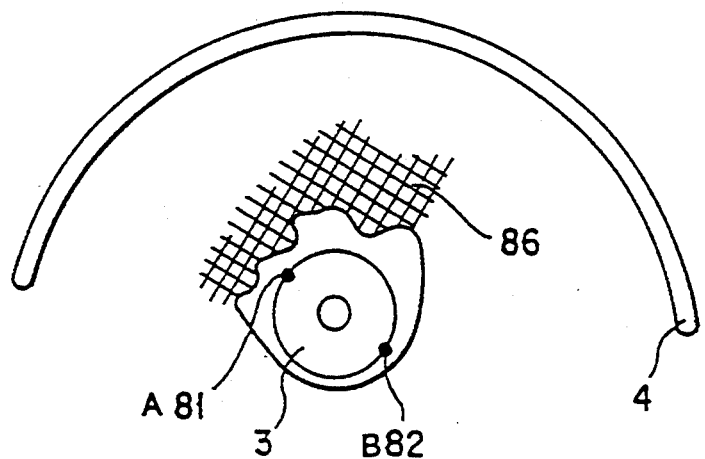
FIG. 24 is a state showing applicators attached to a patient as used in the second embodiment.

FIG. 23 is a flow chart for checking whether or not each temperature sensor is correctly operated. Checking is made to see whether or not the respective sensors are operated or how many sensors are correctly operated. Of importance is $n \geq 2$. The reason for this will be explained below with reference to FIG. 24. FIG. 24 shows a state in which temperature is elevated when an affected region is present at a portion of the cavity organ.

The elevating of the temperature is achieved between the internal applicator 3 and the external applicator 4 with the affected region 36 sandwiched. In this case, the internal applicator 3 has to be positioned in contact with the affected region in the cavity organ. Upon the attachment of the internal applicator, the associated electrode section can be brought nearly to the affected region 86. It is generally, however, difficult to confirm whether or not the temperature sensor just faces the affected area 86 at a location between the internal applicator and the external applicator 4. Let it be assumed that a single temperature sensor is employed. There may sometimes occur the case where an operator starts to elevate temperature when that temperature sensor is placed in a region to be warmed at other than a location between the internal applicator 3 and the external applicator 4.

Upon thermotherapy, confirmation is made to see whether or not two or more temperature sensors can be employed. In this case, it is determined that temperature be not elevated when only one temperature sensor is available. Even if any affected region is located in a manner offset in a direction of the body cavity, at least one temperature sensor can be made to confront the affected region 86 at a location between the internal applicator and the external applicator. By so doing it is possible to positively detect temperature at a region to be warmed and hence to obtain correct temperature information. It is thus possible to treat the affected region at a properly elevated temperature.

Although the affected region has been explained as being warmed through the application of the high-frequency voltage across the electrodes of the paired applicators, the present invention is not restricted thereto. The applicators may be of such a type that they have an antenna for radiating an electromagnetic wave, such as a microwave.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An apparatus for thermotherapy that heats an affected region of a human body to an elevated temperature, comprising:
   (a) applying means for applying a variable, temperature-elevating output to the affected region of the human body;
   (b) temperature measuring means, including a plurality of temperature sensors, for detecting and measuring a plurality of temperatures at a plurality of different sites in a region of said human body that includes, and is larger than, the affected region of the human body, said plurality of temperature sensors being arranged to detect said plurality of temperatures at respective different sites in said region of said human body;
   (c) selecting means for selecting at least one of a plurality of temperature data signals provided by the at least one of the plurality of temperature sensors in accordance with a treatment objective for temperature-elevating the affected region, and for generating a signal corresponding to the selected at least one temperature data signal;
   (d) comparing means for comparing the selected at least one temperature data signal with a plurality of predetermined temperature range data, and for generating a control signal for controlling a temperature-elevating signal responsive to a comparison result of the comparing means;
   (e) control means for controlling the variable, temperature elevating output of the applying means in accordance with the control signal to set the elevated temperature at the affected region of the human body to be within a predetermined temperature range by providing said variable temperature elevating output to said applying means only when said temperature sensed by said at least one sensor is above a minimum value of said predetermined temperature range and below a maximum value of said predetermined temperature range; and (f) display means for displaying the plurality of temperatures measured by the temperature measuring means.

2. The apparatus according to claim 1, wherein:

the selecting means includes means for selecting more than one of the plurality of temperature data signals that are respectively provided by more than one of the plurality of temperature sensors; and the comparing means includes a comparator which compares the selected more than one temperature data signals with the purality of predetermined temperature range data, and the comparing means further includes generating means which generates the control signal responsive to a comparison result of the comparator.

3. The apparatus according to claim 1, wherein the control means, responsive to the control signal, selects one of an increase and a decrease in the temperature-elevating output of the applying means.

4. The apparatus according to claim 3, wherein the applying means includes:

an internal applicator that is placeable inside a body cavity of the human body, the internal applicator having an internal electrode; and an external applicator that is placeable outside the human body, said external applicator having an external electrode; whereby a high-frequency electric field is created at the region of the human body, including the affected region, by an application of a high-frequency voltage across the internal and external electrodes to thereby elevate a temperature at the affected region to be within the predetermined temperature range.

5. The apparatus according to claim 3, wherein the applying means includes an applicator having a generator for generating a high frequency voltage that creates an electromagnetic wave that heats the affected region of the human body.

6. The apparatus according to claim 1, wherein the applying means include:

an internal applicator that is placeable inside a body cavity of the human body, the internal applicator having an internal electrode; and an external applicator that is placeable outside the human body, said external applicator having an external electrode; whereby, when a high-frequency electric field is created in the region of the human body, including the affected region, by an application of a high-frequency voltage across the internal and external electrodes, a temperature at the affected region is elevated to be within the predetermined temperature range.

7. The apparatus according to claim 6, further comprising:

cooling apparatus for preventing an overheating of the internal applicator, the cooling apparatus including:

a coolant passage connected to the internal applicator, a coolant being provided in the coolant passage; and a pump connected to the coolant passage for pumping the coolant in the coolant passage to the internal applicator so as to cool the internal applicator.

8. The apparatus according to claim 7, further comprising coolant temperature control means for controlling a temperature of the coolant that is supplied to the coolant passage of the cooling means.

9. The apparatus according to claim 6, wherein the applying means includes an applicator having a generator for generating and applying the high frequency voltage across the internal and external electrodes that creates the high-frequency electric field that heats the affected region of the human body.

10. The apparatus according to claim 1, wherein at least one of the plurality of temperature sensors, other than the one temperature sensor providing the at least one temperature data signal selected by the selecting means, is an active sensor that provides an output that is usable for monitoring at least one temperature in said region of said human body that is outside said affected region.

11. The apparatus according to claim 1, wherein the control means includes an interruptor, responsive to the control signal, for interrupting the temperature-elevating output of the applying means.

12. The apparatus according to claim 11, wherein the applying means includes an applicator having a generator that generates a high frequency voltage for creating an electromagnetic wave that heats the affected region of the human body.

13. The apparatus according to claim 11, wherein the applying means includes:

an internal applicator that is placeable inside a body cavity of the human body, said internal applicator having an internal electrode; and an external applicator that is placeable outside the human body, said external applicator having an external electrode; whereby, when a high-frequency electric field is created in the region of the human body, including the affected region, by an application of a high-frequency voltage across the internal and external electrodes, a temperature at the affected region is elevated to be within the predetermined temperature range.

14. A method for heating an affected region of a human body and for thermally treating the affected region to provide thermotherapy for the affected region, comprising the steps of:

(a) thermally elevating a temperature of the affected region of the human body to an elevated temperature;

(b) individually detecting a plurality of temperatures at a plurality of sites in the human body, with a plurality of temperature sensors which are arranged in a region that is larger than and includes the affected region of the human body;

(c) selecting at least one of a plurality of temperature data signals provided by respective ones of the plurality of temperature sensors in accordance with a treatment objective for temperature-elevating the affected region, and generating at least one signal corresponding to the selected at least one temperature data signal;

(d) comparing the selected at least one of the plurality of temperature data signals with a plurality of predetermined temperature range data, and generating a control signal for controlling a temperature-elevating signal;

(e) controlling thermal elevation of the affected region in accordance with the control signal and for setting the temperature at the affected region of the human body to be within a predetermined temperature range by providing said control signal only when said temperature sensed by said at least one sensor is above a minimum value of said predetermined temperature range and below a maximum value of said predetermined temperature range; and displaying the plurality of temperatures measured by the plurality of temperature sensors at the plurality of sites in the human body.

* * * * *